(12) United States Patent
Kralj et al.

(10) Patent No.: US 8,389,505 B2
(45) Date of Patent: Mar. 5, 2013

(54) ADAMANTANE DERIVATIVES OF AZA-CROWN ETHERS AND THEIR USE IN TREATMENT OF TUMOR

(75) Inventors: Marijeta Kralj, Zagreb (HR); Kata Majerski, Zagreb (HR); Tatjana Sumanovac Ramljak, Zagreb (HR); Marko Marjanovic, Zagreb (HR)

(73) Assignee: Rudjer Boskovic Institute (HR)

( * ) Notice: Subject to any disclaimer, the term of this patent is extended or adjusted under 35 U.S.C. 154(b) by 0 days.

(21) Appl. No.: 13/107,492

(22) Filed: May 13, 2011

(65) Prior Publication Data

US 2011/0257254 A1    Oct. 20, 2011

Related U.S. Application Data

(63) Continuation of application No. PCT/HR2010/000009, filed on Apr. 9, 2010.

(30) Foreign Application Priority Data

Jun. 19, 2009   (HR) .............................. P 20090355 A

(51) Int. Cl.
    *A61K 31/33*    (2006.01)
    *C07D 273/08*  (2006.01)
(52) U.S. Cl. ........................................ 514/183; 540/474
(58) Field of Classification Search ........................ None
    See application file for complete search history.

(56) References Cited

PUBLICATIONS

Suggitt. Clinical Cancer Research, 2005, 971-981.*
European Journal of Medicinal Chemistry, 2011, 46, 3444-3454.*
Schultz, et al.; "12-, 15-, and 18-Membered-Ring Nitrogen-Pivot Lariat Ethers: Synthesis, Properties, and Sodium and Ammonium Cation Binding Properties"; J. Am. Chem. Soc. 1985; 107; 6659-6668.
Lunn, et al.; "Adamantane Chemistry, Part I. The Synthesis of 1,2-Disubstituted Adamantanes"; J. Chem. Soc. 1968; 1657-1660.
Brandt, et al.; "AIDS-Related Lymphoma Screen Results and Molecular Structure Determination of a New Crown Ether Bearing Aziridinylcyclophosphazene, Potentially Capable of Ion-Regulated DNA Cleavage Action"; Inorganica Chimica Acta 322 (2001); pp. 138-144.
Brown, et al.; "Anticoccidial Activity of Crown Polyethers"; J. Med. Chem. 1983; 26; pp. 590-592 (only p. 590 submitted).
Yagi, et al.; "Antifungal Activity of Crown Ethers"; Journal of Inclusion Phenomena; 2; pp. 179-184; 1984.
Marjanovic, et al.; "Antitumor Potential of Crown Ethers: Structure-Activity Relationships, Cell Cycle Distubances, and Cell Death Studies of a Series of Ionophores" J. Med. Chem. 2007; 1007-1018.
Yavorskaya, et al.; "Antitumor Properties of Actinocin-Based Crown Compounds"; Pharmaceutical Chemistry Journal; 2001; pp. 15-17.
Takayama, et al.; "Apparent Oral Toxicity of 18-Crown-6 in Dogs"; Chem. Pharm. Bull. 1977; p. 3125.

Gad, et al.; "Behavioral and Neuropharmacological Toxicology of Nacrocyclic Ether 18-Crown-6"; Drug and Chemical Toxicology, 1(4), pp. 339-353 (1978).
Kralj, et al.; "Biomedical Potentials of Crown Ethers: Prospective Antitumor Agents"; ChemMedChem 2008; 1478-1492.
Gumila, et al.; "Characterization of the Potent In Vitro and In Vivo Antimalarial Activities of Ionophore Compounds"; Antimicrobial Agents and Chemotherapy , Mar. 1997; pp. 523-529.
Leevy, et al.; "Correlation of Bilayer Membrane Cation Transport and Biological Activity in Alkyl-Substituted Lariat Ethers"; Org. Biomol. Chem. 2005; 1647-1652.
Gokel, et al.; "Crown Ethers: Sensors for Ions and Molecular Scaffolds for Materials and Biological Models" Chem. Rev. 2004; 104; 2723-2750.
Pedersen; "Cyclic Polyethers and Their Complexes with Metal Salts" J. Am. Chem. Soc.; 1967; 7017-7036.
Mlinaric-Majerski, et al.; "Design, Synthesis and Cation-Binding Properties of Novel Adamantane- and 2-Oxaadamantane-Containing Crown Ehters"; Tetrahedron; 2001; 449-457.
Biron, et al.; "Design, Synthesis, and Characterization of Peptide Nanostructures Having Ion Channel Activity"; Bioorganic & Medicinal Chemistry 12 (2004); pp. 1279-1290.
Ranganathan, et al.; "Diamond Crowns: Designs, Synthesis and X-Ray Crystallographic Studies of a Novel Family of Adamantane-Containing Crown Ethers" Tetrahedron; 1999; 6643-6656.
Oppolzer, et al. "Enantioselective systheses of [alpha]-amino acids from 10-sulfonamido-isobornyl esters and di-t-butyl azodicarboxylate"; Tetrahedron 1988, 44, 5541-5552.
Tso, et al.; "Intracellular Potassium Level: Possible Trigger for Bacterial Logarithmic Growth"; Inorganica Chimica Acta; 1980; L33-L34.
International Search Report; Application No. PCT/HR2010/000009; Issued: Sep. 7, 2010; Mailing Date: Sep. 23, 2010; 2 pages.
lzv. Akad. Nauk SSSR Ser. Khim., 1984, 2028-2036.
Gokel; "Lariat Ethers: From Simple Sidearms to Supramolecular Systems"; Chemical Society Reviews; 1992; 39-47.
Hancock; "Ligand Design for Selective Complexation of Metal Ions in Aqueous Solution"; Chem. Rev. 1989; 1875-1914 (one page).
Fukuda, et al; "Metal Ion Assisted DNA-Intercalation of Crown Ether-Linked Acridine Derivatives"; J. Chem. Soc., Chem. Commun, 1990; pp. 1028-1030.
Mlinaric-Majerski, et al.; "Molecular structure of bis[(1,3)2-oxaadamantano]-18-crown-6 and its potassium picrato complex"; Journal of Molecular Structure; vol. 554, Issues 2-3, Nov. 7, 2000, pp. 279-287.

(Continued)

*Primary Examiner* — Noble Jarrell
(74) *Attorney, Agent, or Firm* — St. Onge Steward Johnston & Reens LLC

(57) ABSTRACT

The invention relates to adamantane diaza-crown ether derivatives and the use of mono and diaza-crown ether adamantine derivatives in treatment, especially in tumor treatment. Adamantane aza-crown ethers were obtained by reaction of the corresponding adamantane derived tosylates or adamantane acid chlorides with mono- and diaza-18-crown-6. The prepared compounds showed moderate (monoaza-18-crown-6) to strong (diaza-18-crown-6) antiproliferative and cytotoxic activity on several tumor cell lines, revealing their potential for inhibiting the growth of other tumor cells.

10 Claims, No Drawings

PUBLICATIONS

Frühauf, et al; "New Platinum, Titanium, and Ruthenium Complexes with Different Patterns of DNA Damage in Rat Ovarian Tumor Cells"; Cancer Research 51, pp. 2943-2948, Jun. 1, 1991.

Marchand, et al.; "Novel Cage-Annulated Crown Ethers, Cryptands, and Molecular Boxes: A New Class of Ionophores for Selective Ion Complexation"; 2001; 129-138.

Hendrixson, et al.; "Oral Toxicity of the Cyclic Polyethers—12-Crown-4, 15-Crown-5, and 18-Crown-6—In Mice"; Toxicology and Applied Pharmacology 44, pp. 263-268 (1978).

Naemura, et al.; "Preparation of homochiralcrownether containing (S)-1-(1-adamantyl)ethane-1,2-diol as a chiral subunit and its enantioselective complexation with an organic ammonium cation"; Tetrahedron: Asymmetry vol. 5, Issue 8, Aug. 1994, pp. 1549-1558.

McPhee, et al.; "Propargylic Sulfone-Armed Lariat Crown Ethers: Alkali Metal Ion-REgulated DNA Cleavage Agents"; Bioorganic Chemistry; 2000; 98-118.

Karawajew, et al.; "Role of Crown-Like Side Chains in the Biological Activity of Substituted-Phenoxazone Drugs"; Anti-Cancer Drug Design (2000), 15, pp. 331-338.

Henkel, et al.;"Structure-Anti-Parkinson Activity Relationships in the Aminoadamantanes, Influence of Bridgehead Substitution"; J. Med. Chem. 1982; 51-56.

Gatto, V. J.; Arnold, K. A.; Viscariello, A. M.; Miller, S. R.; Morgan, C. R.; Gokel, G. W.; "Syntheses and Binding Properties of Bibracchial Lariat Ethers (BiBLEs): Survey of Synthetic Methods and Cation Selectivities," J. Org. Chem. 1986, 51, 5373-5384.

Gokel, et al.; "Syntheses of Aliphatic Azacrown Compounds"; Synthesis 1982; 1982(12): 997-1012.

Mlinaric-Majerski, et al.; "Synthesis and alkali metal binding properties of novel N-adamantylaza-crown ethers"; Tetrahedron (2002) vol. 58, Issue: 24, pp. 4893-4898.

Marchand, et al.; "Synthesis and alkali metal picrate extraction capabilities of a 4-oxahexacyclo[5.4.1.0$^2$,$^6$.0$^3$,$^{10}$.0$^5$,$^9$.0$^8$,$^{11}$]dodecane-derived cryptand. A new ionophore for selective ion complexation"; Tetrahedron Letters vol. 39, Issue 14, Apr. 2, 1998, pp. 1861-1864.

Marchand, et al.; "Synthesis and alkali metal picrate extraction capabilities of novel cage-functionalized 17-crown-5 and 17-crown-6 ethers."

Tobe, et al.; "Synthesis and Lithium Ion Selectivity of 14-Crown-4 Derivatives Having Bulky Subunits: cis and trans Isomers of 2-Phenylcyclohexano-14-Crown-4, 2,3-Diphenylcyclohexano-14-Crown-4 and 2,3-di-(1-Adamantyl)-14-Crown-4" J. Chem. Soc. Perkin Trans; 1998; 485-494.

Krakowiak, et al.; "Synthesis of Aza-Crown Ethers"; Cehm. Rev. 1989; 929-972 (one page).

Eguchi, et al.; "Synthesis of Crown Ethers Embodied Adamantane and Homoadamantane Skeletons (1)"; 1998; 217-226.

McPhee, et al.; "Synthesis, DNA Cleavage, and Cytotoxicity of a Series of Bis(propargylic) Sulfone Crown Ethers"; Biorganic & Medicinal Chemistry; 2001; 2809-2818.

Ihara, et al.; "Synthetic DNA Ligands Conjugated with Metal Binding Moiety. Regulation of the Interaction with DNA by Metal Ions and the Ligand Effect on Metal Assisted DNA Cleaving"; Supramolecular Chemistry; 8:2; pp. 93-111; 1997.

Hirose, et al. "Temperature dependent inversion of enantiomer selectivity in the complexation of optically active azophenolic crown ethers containing alkyl substituents as chiral barriers with chiral amines"; J. Chem. Soc., Perkin Trans. 2, 1997, 1649-1658.

Christensen, et al.; "The Synthesis and Ion Binding of Synthetic Multidentate Macrocyclic Compounds" 1973; p. 351.

Izatt, et al.; "Thermodynamic and Kinetic Data for Cation-Macrocycle Interaction"; Chem. Rev. 1985; 271-339 (one page).

Izatt, et al.; "Thermodynamic and Kinetic Data for Macrocycle Ineraction with Cations, Anions, and Neutral Molecules"; Chem. Rev. 1995; 2529-2586 (one page).

Izatt, et al.; "Thermodynamic and Kinetic Data for Macrocycle Interaction with Cations and Anions"; Chem Rev 1991; 1721-2085 (one page).

Izatt, et al.; "Thermodynamic and Kinetic Data for Macrocycle Interaction with Neutral Molecules"; Chem Rev 1992; 1261-1354 (one page).

Gad, et al; "Thirteen Cationic Ionophores: Their Acute Toxicity, Neurobehavioral and Membrane Effects"; Drug and Chemical Toxicology, 8(6), pp. 451-468 (1985).

Tso, et al.; "Variability of Crown Ether Toxicity"; Journal of Inorganic Biochemistry; 1981; 237-244.

Gokel, G. W.; Dishong, D. M.; Schultz, R. A.; Gatto, V. J.; "Syntheses of Aliphatic Azacrown Compounds"; Synthesis, 1982, 997-1012.

Zh. Ob. Khim., 1987,57,671-675.

Zh. Org. Khim., 1989, 25, 2000-2003.

* cited by examiner

ADAMANTANE DERIVATIVES OF AZA-CROWN ETHERS AND THEIR USE IN TREATMENT OF TUMOR

CROSS-REFERENCE TO RELATED APPLICATIONS

The present application is a continuation of pending International Patent Application PCT/HR2010/000009 filed on Apr. 9, 2010 which designates the United States and claims priority from Croatian Patent Application P20090355A filed on Jun. 19, 2009, the content of which is incorporated herein by reference.

FIELD OF THE INVENTION

The present invention relates to adamantane derivatives of diaza-18-crown-6. Also, the invention relates to the use of adamantane derivatives of diaza-18-crown-6 and monoaza-18-crown-6 in treatment, preferably in tumor treatment.

BACKGROUND OF THE INVENTION

Macrocyclic polyethers have a widespread use in various areas of science and technology ever since the first preparation of the crown ethers by Pedersen. (Pedersen, C. J. *J. Am. Chem. Soc.* 1967, 89, 7017.) In the research oriented towards crown ethers a special emphasis has been directed at finding suitable chemical compounds that can selectively recognize and bind cations. Structural modifications of macrocyclic ligands have been performed, where the size of the macrocyclic ring and the type of donor atoms were changed and cation binding properties were investigated (J. J. Christensen, D. J. Eatough, R. M. Izatt, *Chem. Rev.,* 1974, 74, 351-384.; R. D. Hancock, A. E. Martell, *Chem. Rev.,* 1989, 89, 1875-1914.); synthesis of aza-crown ethers (R. A. Schultz, B. D. White, D. M. Dishong, K. A. Arnold, G. W. Gokel, *J. Am. Chem. Soc.,* 1985, 107, 6659-6668.; K. E. Krakowiak, J. S. Bradshaw, D. J. Zamecka-Krakowiak, *Chem. Rev.,* 1989, 89, 929-972.); synthesis of mono and di-lariat aza-crown ethers (G. W. Gokel, D. M. Dishong, R. A. Schultz, V. J. Gatto, *Synthesis,* 1982, 997-1012.; G. W. Gokel, *Chem. Soc. Rev.,* 1992, 39-47.); synthesis of BiBLE (V. J. Gatto, K. A. Arnold, A. M. Viscariello, S. R. Miller, C. R. Morgan, G. W. Gokel, *J. Org. Chem.,* 1986, 51, 5373-5384.). Various substituents have been introduced and the influence of the structure on the complexing properties of the ligands examined (Lehn, J. M. *Supramolecular Chemistry: Concepts and Perspectives*, VCH, Weinheim, Germany, 1995.).

Presently, it is possible to define accurately the key factors which influence the affinity of a ligand towards a specific cation, and thus to effectively control its selectivity. (Schneider, H. J.; Yatsimirsky, A. *Principles and Methods in Supramolecular Chemistry*, Wiley and Sons, Ltd., Chichester, UK, 2000. Steed, J. W.; Atwood, J. L. *Supramolecular Chemistry*, Wiley & Sons, LTD. Chichester, UK, 2000. Vögtle, F. *Supramolecular Chemistry*, Wiley, New York, 1991.). For instance, there are several reviews describing interactions between the cations and macrocyclic compounds (J. J. Christensen, D. J. Eatough, R. M. Izatt, *Chem. Rev.,* 1974, 74, 351-384. R. M. Izatt, J. S. Bradshaw, S. A. Nielsen, J. D. Lamb, J. J. Christensen, *Chem. Rev.,* 1985, 85, 271-339.); cation and anion interactions with macrocyclic molecules (R. M. Izatt, K. Pawlak, J. S. Bradshaw, R. L. Bruening, *Chem. Rev.,* 1991, 91, 1721-2085.); interactions of neutral molecules with macrocyclic compounds (R. M. Izatt, J. S. Bradshaw, K. Pawlak, R. L. Bruening, *Chem. Rev.,* 1992, 92, 1261-1354.); or interactions of all above mentioned categories, cations, anions and neutral molecules with macrocyclic crown ethers (R. M. Izatt, K. Pawlak, J. S. Bradshaw, *Chem. Rev.,* 1995, 195, 2529-2586. G. W. Gokel, W. M. Leevy, M. E. Weber, *Chem. Rev.,* 2004, 104, 2723-2750.).

Nevertheless, there are little or no publications describing the use of the particular class of compounds in antitumor therapy. Although the research on potential biological activity of crown ethers is still in its early stages, their potential impact remains large (M. Kralj, Lj. Tušek-Božić, L. Frkanec, *Chem Med Chem*, 2008, 3:1478-1492 and the references cited therein). From the biological or biomedical point of view, one of the most interesting features of crown ethers is the fact that, due to their ionophoric properties in the membranes, they behave very similarly to natural ionophores, such as gramicidin, valinomycin, nonactin, etc. Naturally occurring ionophores, as metabolites of microorganisms (e.g. *Streptomyces* sp.), disrupt the flow of ions either into or out of the cells, which dissipate the cellular ion gradients leading to physiological and osmotic stress. Bacteria (particularly gram positive bacteria) are very sensitive to this effect. Since cyclic polyethers clearly discriminate among different ions, they can serve as convenient synthetic model compounds for their biological counterparts and have similar functions (G. W. Gokel, W. M. Leevy, M. E. Weber, *Chem. Rev.,* 2004, 104, 2723-2750). Indeed, crown ethers were found to be toxic in prokaryotic and eukaryotic cellular systems which led to further studies on their potential for being developed as pharmacological agents (W. W. Tso, W.-P. Fung, M. Y. Tso, *J. Inorg. Biochem.* 1981, 14, 237-244.) It was shown that certain ionophores have antiparasitic activity (e.g. antimalarial or anticoccidial activity) (C. Gumila, M. L. Ancelin, A. M. Delort, G. Jeminet, H. J. Vial, *Antimicrob. Agents Chemother.* 1997, 41, 523-529.; G. R. Brown, A. J. Foubister, *J. Med. Chem.* 1983, 26, 590-592.), therefore efforts have been made to prepare efficient crown compounds with potential antiparasitic activity. In addition, certain crown ethers were found to have significant antifungal activity against some wood-decay fungi, phytopathogenic fungi, eumycetes and trichophytons for dermatomycosis. Yagi and co-workers found that among the 26 crown ethers tested 3,5-di-t-butyl-benzo-15-crown-5 showed relatively high activity, while unsubstituted crown compounds or those with a polar substituent were inactive (K. Yagi, V. Garcia, M. E. Rivas, J. Salas, A. Camargo, T. Tabata, *J. Incl. Phenom. Macrocycl. Chem.* 1984, 2, 179-184.). Tso and co-workers found that substituted 18-crown-6 ethers show different inhibitory effects on the growth of *E. Coli* (W. W. Tso, W.-P. Fung, M. Y. Tso, *J. Inorg. Biochem.* 1981, 14, 237-244.; W. W. Tso, W.-P. Fung, *Inorg. Chim. Acta* 1980, 46, L33-L34). Thereafter, various approaches were developed to prepare crown-based antimicrobial agents. Leevy and co-workers determined minimal inhibitory concentrations of several alkyl-substituted lariat ethers on *E. coli, B. subtilis* and yeast (W. M. Leevy, M. E. Weber, M. R. Gokel, G. B. Hughes-Strange, D. D. Daranciang, R. Ferdani, G. W. Gokel, *Org. Biomol. Chem.* 2005, 3, 1647-1652.). The authors proposed the mechanism for toxicity. It depends on the ability of these compounds to transport ions, most probably by inserting and integrating into membrane bilayer and conducting cations as expected for carriers, whereby the side chain length and hydrophobicity play an essential role. Sensitivity to various compounds varied among the tested organisms, depending on the membrane structures. Furthermore, numerous approaches were developed to build more complex synthetic ion transporters with potential biological activity—the channels such as crown ether peptide nanostructures having ion channel or hydrophile activity (G. W. Gokel, W. M. Leevy, M.

E. Weber, *Chem. Rev.*, 2004, 104, 2723-2750; E. Biron, F. Otis, J.-C. Meillon, M. Robitaille, J. Lamothe, P. Van Hove, M.-E. Cormier, N. Voyer, Bioorg. Med. Chem. 2004, 12, 1279-1290).

Biological Activity in Mammalian Cells

Immediately after the crown ethers were discovered, their toxic effect to higher organisms was observed. More than 20 years ago various studies have been performed showing toxicity of different cationic ionophores (including crown ethers) in multiple species, such as mice, rats and dogs (K. Takayama, S. Hasegawa, S. Sasagawa, N. Nambu, T. Nagai, *Chem. Pharm. Bull.* 1977, 25, 3125-3130.; S. C. Gad, W. J. Conroy, J. A. McKelvey, K. A. Turney, *Drug Chem. Tox.* 1978, 1, 339-353.; R. R. Hendrixon, M. P. Mack, R. A. Palmer, A. Ottolenghi, R. G. Ghirardelli, *Toxicol. Appl. Pharmacol.* 1985, 8, 451-468.; S. C. Gad, C. Reilly, K. Siino, F. A. Gavigan, G. Witz, *Drug Chem. Tox.* 1985, 8, 451-468.). These studies have clearly shown that the majority of the ionophores induced neurotoxic effects of reversible pharmacological nature. Crown compounds have also shown neither to be genotoxic nor mutagenic (M. Kralj, Lj. Tušek-Božić, L. Frkanec, *ChemMedChem*, 2008, 3:1478-1492).

However, although their cytotoxic effects on mammalian cells (including tumor cells) were soon recognized, no systematic studies were performed on the potential antitumor ability of crown ether compounds. The exceptions are functionalized crown ethers synthetically designed to interact with DNA: e.g. to alkylate and/or cleave DNA in order to achieve antitumor activity (M. Kralj, Lj. Tušek-Božić, L. Frkanec, *ChemMedChem*, 2008, 3:1478-1492). The emphasis was put on the mutual effect of two functionally different parts: e.g. one part carries a DNA intercalating function, while the other has an ability to bind metal ions. Thus, the DNA binding ability of such compounds should be influenced or regulated by metal ions complexation, since metal complexation should lead to the change in the net electric charge along with the change in the ligand conformation (T. Ihara, S. Sueda, A. Inenaga, R. Fukuda, M. Takagi, *Supramol. Chem.* 1997, 8, 93-111). DNA binding and intercalation studies were performed with different crown compounds having various side arms, such as crown ether linked DNA-intercalators (e.g. acridine or antraquinone derivatives). In these studies the acridine subunit binds to DNA while the crown subunit binds cations which interact with the phosphate DNA backbone, thus stabilizing the complex (R. Fukuda, S. Takenaka, M. Takagi, *J. Chem. Soc., Chem. Commun.* 1990, 1028-1030). Furthermore, crown ether derivatives of actinomycin D (AMD) containing benzo-15-crown-5 and benzo-18-crown-6 groups attached via amide bonds were also described and tested in human and mouse tumor model systems (L. Karawajew, E. N. Glibin, V. Ya. Maleev, G. Czerwony, B. Dörken, D. B. Davies, A. N. Veselkov, *Anti-Cancer Drug Des.* 2000, 15, 331-338.; N. P. Yavorskaya, I. S. Golubeva, I. Yu. Kubasova, A. V. Ovchinnikov, N. G. Plekhanova, E. N. Glibin, *Pharm. Chem. J.* 2001, 35, 305-307.).

Some functionalized crown compounds were designed to covalently modify (alkylate) and cleave DNA in the ion-regulated manner. Two groups of researchers developed compounds that alkylate and cleave DNA and also stops the tumor cell growth (K. Brandt, R. Kruszynksi, T. J. Bartczak, I. Porwolik-Czomperlik, *Inorg. Chim. Acta* 2001, 322, 138-144.; M. M. McPhee, J. T. Kern, B. C. Hoster, S. M. Kerwin, *Bioorg. Chem.* 2000, 8, 98-118.; M. M. McPhee, S. M. Kerwin, *Bioorg. Med. Chem.* 2001, 9, 2809-2818). For example, compounds having aziridinyl groups introduced in the crown-bearing cyclotriphosphazene, such as tetraaziridinyl-lariat ethers, were tested for in vitro antitumor activity in an investigational AIDS-related lymphoma screening. As a result of synergistic effects from the interaction of metal and (di)alkylating aziridinyl with DNA, this compound showed remarkable cytostatic activity. The DNA damage stops cell proliferation, making this compound a cytostatic drug (K. Brandt, R. Kruszynksi, T. J. Bartczak, I. Porwolik-Czomperlik, *Inorg. Chim. Acta* 2001, 322, 138-144).

Propargylic sulphone-armed lariat crown ethers and bis (propargylic) sulfone crown ethers were prepared in order to causal connect molecular recognition of specific alkali metal ions to DNA damage under conditions of elevated alkali metal ion levels reported to exist in tumor cells. These compounds were tested against tumor cell growth inhibition at the National Institute of Health, National Cancer Institute, some of them showing significantly more pronounced DNA cleavage and cytotoxic activity compared to the non-crown ether analogues (M. M. McPhee, J. T. Kern, B. C. Hoster, S. M. Kerwin, *Bioorg. Chem.* 2000, 8, 98-118.; M. M. McPhee, S. M. Kerwin, *Bioorg. Med. Chem.* 2001, 9, 2809-2818). Also, platinum-based DNA-binding/alkylating agents containing crown ether moiety were prepared and tested for potential antitumor activity. The antitumor effect of platinum compounds is ascribed to the reaction of platinum atom with nucleophilic DNA sites, whereby major adducts and intrastrand cross-links are formed by binding of cisplatin to two neighbouring guanines. An example of potential platinum antitumor compound having platinum atoms linked through a spacer or pendant coordinating groups is 18-crown-6-tetra-carboxybis-diammineplatinum(II). Its antitumor activity is tested in different tumor models and in general corresponds to cisplatin activity in cisplatin-sensitive as well as in cisplatin-resistant cells. Moreover, its toxicity in vivo is considerably lower (S. Frühaufand, V. J. Zeller, *Cancer Res.* 1991, 51, 2943-2948.).

Above mentioned examples show attempts to prepare potential antitumor and other biologically active compounds in which crown ethers, as a part of the molecule, facilitate or enhance the inherent feature (mode of action) of the other part(s) of the same compound. However, as previously mentioned, no systematic study was performed on the antitumor potential of non-functionalized crown compounds. Interestingly, in none of the experiments described above crown ethers were tested in parallel with the crown ether substituted derivatives in order to assess their independent activity. In general, there are limited reports about antiproliferative activity of crown ethers in mammalian cells. Possible antiproliferative/antitumor activity of conventional crown ethers and their derivatives was recently studied and compared to valinomycin. Various derivatives of 18-crown-6 compounds were chosen, as most frequently studied crown ether compounds, along with one 15-membered ring derivative and two derivatives with larger macrocyclic rings: dibenzo-24-crown-8 and dibenzo-30-crown-10. All of them, except the crown ether with the smallest ring, preferred potassium over sodium ion complexation. The results clearly revealed that crown ethers have remarkable tumor-cell growth inhibitory activity and that this activity strongly correlates to both the type of hydrophilic cavity (the size and the nature of donor atoms) and the characteristics of surrounding hydrophobic ring (M. Marjanović, M. Kralj, F. Supek, L. Frkanec, I. Piantanida, T. Šmuc, Lj. Tušek-Božić, *J. Med. Chem.* 2007, 50, 1007-1018.). This work clearly demonstrated the great importance of substituents to this effect, which is enhanced by increasing the hydrophobicity possibly due to requirements for membrane insertion. Nevertheless, neither the lipophilicity nor the $K^+$ binding constants exhibit a linear relationship to antiproliferative activity, indicating that a combination of various molecular properties determine their biological activity.

Although numerous examples of adamantane derivatives of crown ethers are known (A. P. Marchand, K. A. Kumar, A. S. McKim, K. Mlinarič-Majerski, G. Kragol, *Tetrahedron*, 1997, 53, 3467-3474.; K. Mlinarič-Majerski, G. Kragol, *Tetrahedron*, 2001, 57, 449-457.; K. Mlinarič-Majerski, A. Viš- njevac, G. Kragol, B. Kojič-Prodič, *J. Mol. Struct.*, 2000, 554, 279-287.; A. P. Marchand, S. Alihodžić, A. S. McKim, K. A. Kumar, K. Mlinarič-Majerski, T. Šumanovac, S. G. Bott, *Tetrahedron Lett.*, 1998, 39, 1861-1864.; A. P. Marchand, K. A. Kumar, A. S. McKim, S. Alihodžić, H.-S. Chong, K. Krishnudu, M. Takhi, K. Mlinarič-Majerski, G. Kragol, T. Šumanovac, *Kem. Ind.*, 2001, 50, 129-138.; O. A. Raevski, V. V. Tkačev, L. O. Amovman, I. O. Umarova, A. F. Solomonov, T. N. Kundra, A. A. Čajkovskaja, *Izv. Akad. Nauk SSSR Ser. Khim.*, 1984, 2028-2036.; A. A. Čajkovskaja, T. N. Kundra, A. M. Pinčuk, *Zh. Ob. Khim.*, 1987, 57, 671-675. A. A. Čajkovskaja, T. N. Kundra, A. M. Pinčuk, *Zh. Org. Khim.*, 1989, 25, 2000-2003.; K. Naemura, T. Mizo-oku, K. Kamada, K. Hirose, Y. To be, M. Sawada, M. Takai, *Tetrahedron:Asymmetry*, 1994, 5, 1549-1558.; K. Hirose, J. Fuji, J. Kamada, Y. To be, K. Naemura, *J. Chem. Soc., Perkin Trans.* 2, 1997, 1649-1657.; Y. To be, Y. Tsuchiya, H. Iketani, K. Naemura, K. Kobiro, M. Kaji, S. Tsuzuki, K. Suzuki, *J. Chem. Soc., Perkin Trans.* 1, 1998, 485-494.: S. Eguchi, H. Miyake, A. Gupta, T. Okano, *Heterocycl. Commun.*, 1998, 4, 217-226) there are only few reports on adamantane aza-crown ethers (D. Ranganathan, V. Haridas, I. L. Karle, *Tetrahedron*, 1999, 55, 6643-6656.; K. Mlinarič-Majerski, T. Šumanovac Ramljak, *Tetrahedron*, 2002, 58, 4893-4898). The syntheses of the compounds of type II, which are the subject matter of the present invention, and their extraction and binding properties towards alkali metal cations were described in our earlier report (K. Mlinarič-Majerski, T. Šumanovac Ramljak, *Tetrahedron*, 2002, 58, 4893-4898.), but no biological activity was investigated up to now.

SUMMARY OF THE INVENTION

The subject of the present invention is adamantane derivatives of diaza-18-crown-6. Also, the subject of the present invention is the use of adamantane derivatives of mono- and diaza-18-crown-6 in treatment, preferably in tumor treatment.

DETAILED DESCRIPTION OF THE INVENTION

The subject of the present invention is adamantane derivatives of diaza-crown ethers represented by general formula I:

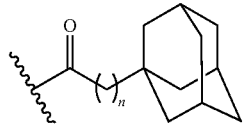

I wherein
R and R' are independently selected from the group comprising

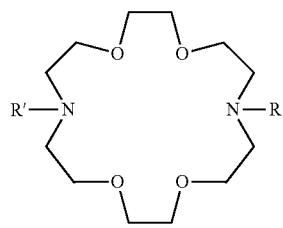

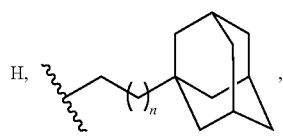

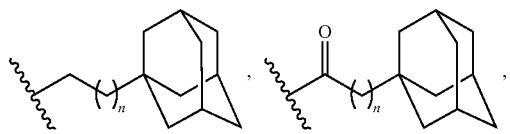

provided that R and R' cannot simultaneously be H;
and n is an integer from 1 to 4.

In the preferred embodiment of the present invention R equals R', and they are selected from the group comprising

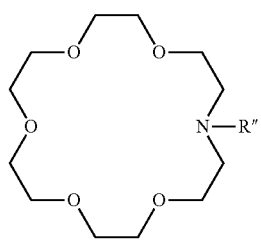

where n is an integer from 1 to 2.

Since the experiments in present invention showed that the adamantane derivatives of mono- and diaza-crown ethers have pronounced biological activity, further subject of the present invention is adamantane derivatives of monoaza-crown ethers represented by general formula II:

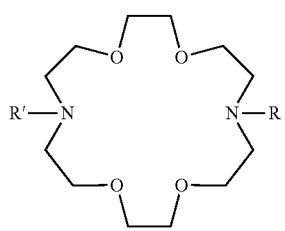

II wherein
R" is selected from the group comprising

and n is an integer from 1 to 4,
and pharmaceutically acceptable salts thereof, where said compounds are used as a medicament.

Furthermore, the subject of the present invention is adamantane derivatives of diaza-crown ethers represented by general formula I:

I wherein
R and R' are independently selected from the group comprising

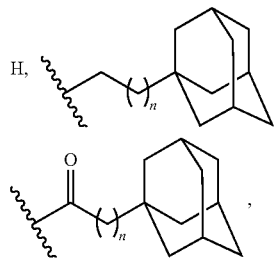

provided that R and R' cannot simultaneously be H;
and n is an integer from 1 to 4,
and pharmaceutically acceptable salts thereof, where said compounds are used as a medicament.

Furthermore, the subject of present invention is compounds represented by general formula II

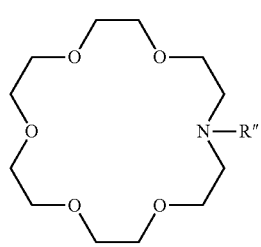

II wherein
R'' is selected from the group comprising

and n is an integer from 1 to 4,
and pharmaceutically acceptable salts thereof, where said compounds are for use in treatments of cancer and tumors.

In the preferred embodiment of said compound of general formula II, n is an integer from 1 to 2.

Moreover, the subject of present invention is compounds represented by general formula I

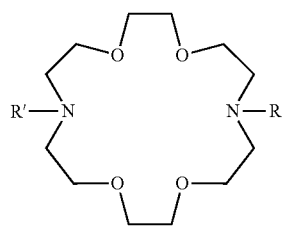

I wherein
R and R' are independently selected from the group comprising

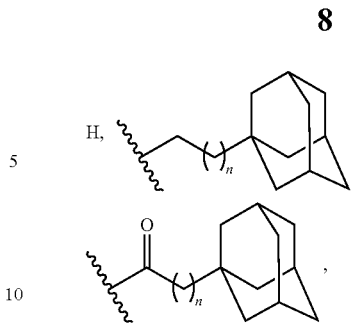

provided that R and R' cannot simultaneously be H;
and n is an integer from 1 to 4,
and pharmaceutically acceptable salts thereof, where said compounds are for use in treatment of cancer and tumors.

In the preferred embodiment of said compound of general formula I, R equals R' and both are selected from the group comprising

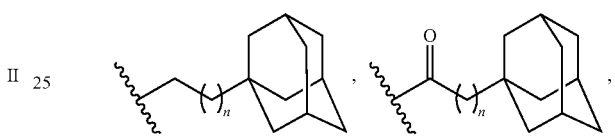

n is an integer from 1 to 2.
In the further preferred embodiment of said compound having general formula I,
R and R' are

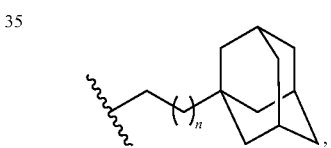

and n is an integer from 1 to 2.

All the above stated compounds of general formula I and II will be used for the production of medicaments for treatment of cancer and tumors.

Furthermore, the subject of the present invention is pharmaceutical compositions comprising at least one of herein described compounds represented by general formula I and II, for use in tumor treatment.

The process of preparation of adamantane derivatives of aza-crown ethers can be carried out in the following manners:

a) coupling reactions of mono- or diaza-18-crown-6 with corresponding adamantane derivatives, 1-(2-tosyloxyethyl) adamantane (J. G. Henkel, J. T. Hane, *J. Med. Chem.*, 1982, 25, 51-56.) and 1-(3-tosyloxypropyl)adamantane (K. Mlinarič-Majerski, T. Šumanovac Ramljak, *Tetrahedron*, 2002, 58, 4893-4898.); or b) coupling reactions of mono- or diaza-18-crown-6 with the corresponding adamantane acid chloride, 1-(chloroethanoyl)adamantane (W. H. Lunn, W. D. Podmore, S. S. Szinai, *J. Chem. Soc.* (C) 1968, 1657-1660.), and 1-(chloropropanoyl)adamantane (W. Oppolzer, R. Moretti, *Tetrahedron*, 1988, 44, 5541-5552.), where amide derivatives that can be further reduced to corresponding amine derivatives with hydride type reagents, in particular $NaBH_4$, $B_2H_6$, or $BH_3$ THF complex, are produced (SCHEMES 1 and 2).

Scheme 1. Syntheses of the compounds represented by general formula I.

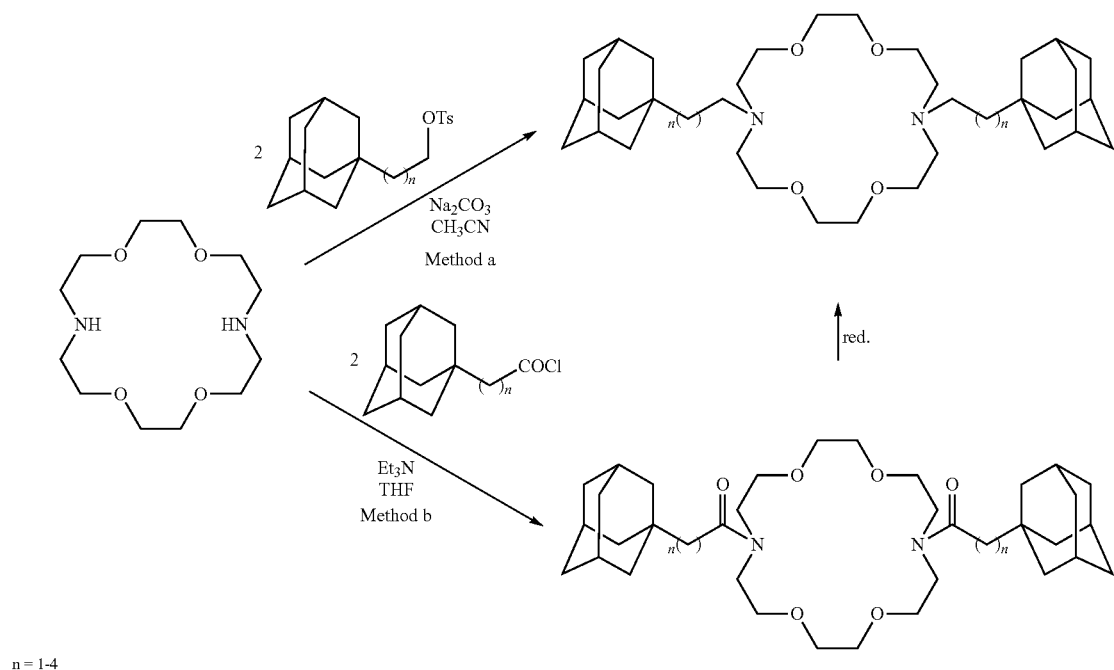

n = 1-4

Scheme 2. Syntheses of the compounds represented by general formula II.

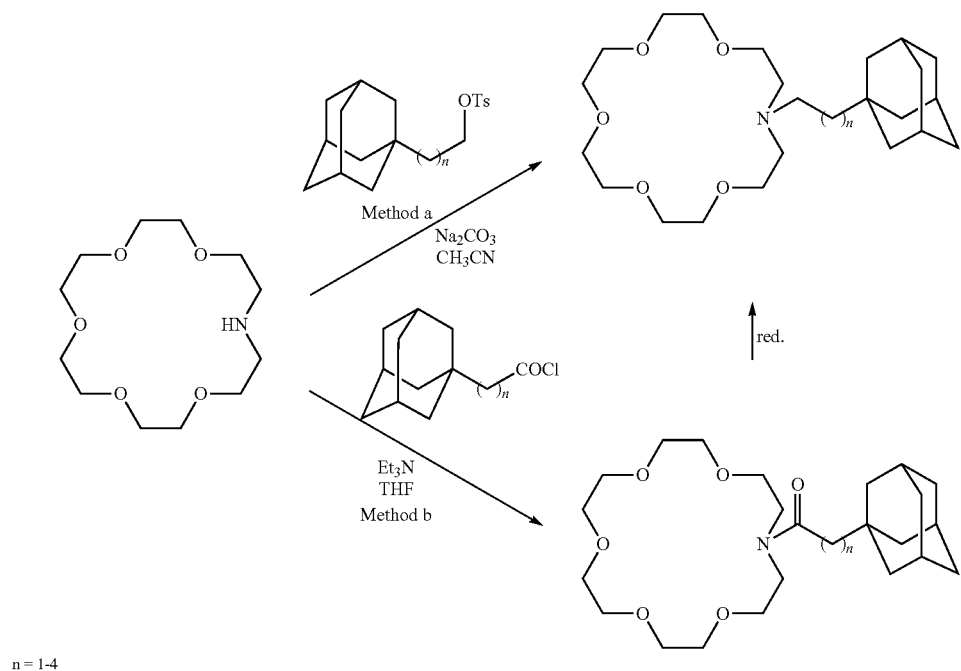

n = 1-4

General procedure for the preparation of adamantane derivatives of aza-18-crown-6 represented by general formulae I and II Method a) In a reaction vessel under a stream of inert gas, $N_2$ or Ar, one or two equivalents of corresponding tosylate and one equivalent of corresponding aza-18-crown-6 were dissolved or suspended in the appropriate anhydrous solvent: acetonitrile, THF, DME, glyme, diglyme, or DMF, DMSO and particularly acetonitrile. To the stirred reaction mixture minimally four equivalents of base were added. The bases used herein comprise $Na_2CO_3$, $K_2CO_3$, $CsCO_3$ and preferably $Na_2CO_3$. The reaction mixture was heated at elevated temperature, preferably at 80° C., for two to five days, after which the reaction mixture was cooled to room temperature and concentrated under reduced pressure. The solid residue was suspended in appropriate solvent $CH_2Cl_2$, glyme or diglyme, preferably $CH_2Cl_2$, and filtered through a plug of celite. The combined filtrates were concentrated under reduced pressure to yield oily product. If needed, the product was additionally purified by column chromatography.

Method b) In a reaction vessel under a stream of inert gas, $N_2$ or Ar, one equivalent of corresponding aza-18-crown-6 was dissolved or suspended in the appropriate anhydrous solvent comprising the following: THF, glyme, diglyme, or DMF, DMSO and particularly THF, and minimally 2.5 equivalents of base (triethylamine or pyridine) was added. The resulting mixture was stirred at room temperature for 10 min and a solution or suspension of corresponding acyl chloride (one or two equivalents) was added. The reaction mixture was stirred at room temperature for additional 24 hours, filtered and the filtrate was evaporated under reduced pressure. The solid residue was suspended in appropriate solvent ($CH_2Cl_2$, glyme or diglyme, preferably $CH_2Cl_2$), washed with saturated solution of NaCl and dried over anhydrous $MgSO_4$ or $Na_2SO_4$. After removal of the solvent under reduced pressure, oily product was obtained. When needed, the product was additionally purified by column chromatography.

General Reduction Procedure

In a reaction vessel under a stream of inert gas, $N_2$ or Ar, one equivalent of obtained adamantane derivative of crown ether was dissolved or suspended in the appropriate anhydrous solvent (THF, ether). The reaction mixture was cooled with ice cooling bath. Two equivalents of diborane solution in THF were added drop wise to the stirred solution. After the addition was completed the ice bath was removed and the temperature was allowed to raise to room temperature. The reaction mixture was stirred under reflux temperature over night. After cooling to room temperature, the excess of diborane was destroyed by slow addition of methanol or water. Hydrochloric acid was added and the reaction mixture was stirred for additional 10 minutes. Organic solvents were removed using rotary evaporator. The solid residue was suspended in $CH_2Cl_2$ and washed with diluted hydrochloric acid. Solid potassium hydroxide was added to the aqueous layer to raise pH above 12. The aqueous layer was extracted with $CH_2Cl_2$. The combined organic extracts were concentrated under reduced pressure to yield oily product. If needed, the product was additionally purified by column chromatography.

Examples 1-4

(These adamantane crown ether derivatives are described in the following document: K. Mlinarič-Majerski, T. Šumanovac Ramljak, *Tetrahedron*, 2002, 58, 4893-4898.)
1 N-[2-(1-adamantyl)ethyl]-aza-18-crown-6
2 N-[3-(1-adamantyl)propyl]-aza-18-crown-6
3 N-[1-oxo-2-(1-adamantyl)ethyl]-aza-18-crown-6
4 N-[1-oxo-3-(1-adamantyl)propyl]-aza-18-crown-6

Example 5

N,N'-Bis[2-(1-adamantyl)ethyl]-4,13-diaza-18-crown-6

By following the general procedure (Method a) the product was obtained via reaction of 1-(2-tosyloxyethyl)adamantane (0.668 g, 0.002 mol) and diaza-18-crown-6 (0.262 g, 0.001 mol). The crude product was purified via column chromatography on $Al_2O_3$ (act. II-III) using 0→2% MeOH in $CH_2Cl_2$ as an eluent thereby yielding 0.317 g (54%) of colourless oily product. An analytically pure sample of N,N"-Bis[2-(1-adamantyl)ethyl]-4,13-diaza-18-crown-6 was obtained by chromatography on a small column of $Al_2O_3$ (act. II-III) using 0→2% MeOH in $CH_2Cl_2$ as an eluent.

IR (KBr) v/cm$^{-1}$: 2903 (s), 2852 (s), 1628 (s), 1462 (m), 1133 (m), 1110 (m), 1096 (m).

$^1$H NMR (CDCl$_3$) δ/ppm: 1.20-1.30 (m, 4H), 1.47 (br. s, 12H), 1.55-1.75 (m, 12H), 1.92 (br. s, 6H), 2.45-2.60 (m, 4H), 2.70-2.85 (m, 8H), 3.55-3.70 (m, 16H).

$^{13}$C NMR (CDCl$_3$) δ/ppm: 28.55 (d, 6C), 31.65 (s, 2C), 37.07 (t, 6C), 40.69 (t, 2C), 42.43 (t, 6C), 49.66 (t, 2C), 53.75 (t, 4C), 69.80 (t, 4C), 70.60 (t, 4C).

HRMS calculated for [$C_{36}H_{62}N_2O_4$+H] 587.4782. Found 587.4758.

Example 6

N,N"-Bis[3-(1-adamantyl)propyl]-4,13-diaza-18-crown-6

By following the general procedure (Method a) the compound was obtained via reaction of 1-(2-tosyloxypropylyl)adamantane (1.50 g, 0.0043 mol) and diaza-18-crown-6 (0.563 g, 0.0022 mol). The crude product was purified via column chromatography on $Al_2O_3$ (act. II-III) using 0→2% MeOH in $CH_2Cl_2$ as an eluent, thereby yielding 0.783 g (59%) of colourless oily product. An analytically pure sample of N,N'-Bis[3-(1-adamantyl)propyl]-4,13-diaza-18-crown-6 was obtained by chromatography on a small column of $Al_2O_3$ (act. II-III) using 0→2% MeOH in $CH_2Cl_2$ as an eluent.

IR (KBr) v/cm$^{-1}$:2901 (s), 2845 (s), 1645 (s), 1450 (m), 1119 (m).

$^1$H NMR (CDCl$_3$) δ/ppm: 0.95-1.05 (m, 4H), 1.35-1.40 (m, 4H), 1.42 (br. s. 12H), 1.60-1.75 (m, 12H), 1.93 (br. s, 6H), 2.40-2.50 (m, 4H), 2.75-2.80 (m, 8H), 3.50-3.70 (m, 16H).

$^{13}$C NMR (CDCl$_3$) δ/ppm: 20.09 (t, 2C), 28.66 (d, 6C), 32.06 (s, 2C), 37.16 (t, 6C), 42.12 (t, 2C), 42.43 (t, 6C), 53.81 (t, 4C), 56.92 (t, 2C), 69.91 (t, 2C), 70.65 (t, 6C).

HRMS calculated for [$C_{38}H_{66}N_2O_4$+H] 615.5095. Found 615.5085.

Example 7

N,N'-Bis[1-oxo-2-(1-adamantyl)ethyl]-4,13-diaza-18-crown-6

By following the general procedure, (Method b) the compound was obtained via reaction of diaza-18-crown-6 (0.68 g, 0.0026 mol) with 1-(chloroethanoyl)adamantane (1.10 g, 0.0052 mol). The crude product was purified via column chromatography on $Al_2O_3$ (act. II-III) using 0→2% MeOH in $CH_2Cl_2$ as an eluent, thereby yielding 0.861 g (56%) of colourless oily product. An analytically pure sample of N,N'-Bis[1-oxo-2-(1-adamantyl)ethyl]-4,13-diaza-18-crown-6 was obtained by chromatography on a small column of $Al_2O_3$ (act. II-III) using 0→2% MeOH in $CH_2Cl_2$ as an eluent.

IR (KBr) v/cm$^{-1}$: 2905 (s), 2845 (s), 1449 (m), 1351 (m), 1126 (s).

$^1$H NMR (CDCl$_3$) δ/ppm: 1.62-1.72 (m, 24H), 1.97 (br. s, 6H), 2.12 (s, 4H), 3.50-3.70 (m, 24H).

$^{13}$C NMR (CDCl$_3$) δ/ppm: 28.38 (d, 6C), 33.37 (s, 2C), 36.54 (t, 6C), 42.42 (t, 6C), 45.48 (t, 1C), 45.56 (t, 1C), 46.33 (t, 1C), 46.57 (t, 1C), 48.97 (t, 1C), 49.18 (t, 1C), 68.97 (t, 1C), 69.63 (t, 1C), 69.81 (t, 1C), 70.08 (t, 1C), 70.22 (t, 1C), 70.39 (t, 1C), 70.44 (t, 1C), 70.59 (t, 1C), 171.17 (s, 1C), 171.24 (s, 1C).

Anal. calcd for $C_{36}H_{58}N_2O_6$ (Mr=614.856): C, 70.32; H, 9.51; N, 4.65. Found C, 69.99; H, 9.26; N, 4.64.

HRMS calculated for $[C_{36}H_{58}N_2O_6+H]$ 615.4368. Found 615.4379.

Example 8

N,N'-Bis[1-oxo-3-(1-adamantyl)propyl]-4,13-diaza-18-crown-6

By following the general procedure (Method b) the compound was obtained via reaction of diaza-18-crown-6 (0.63 g, 0.0024 mol) with 1-(chloropropanoyl)adamantane (1.09 g, 0.0048 mol). The crude product was purified via column chromatography on $Al_2O_3$ (act. II-III) using 0→2% MeOH in $CH_2Cl_2$ as an eluent, thereby yielding 1.014 g (64%) of colourless oily product. An analytically pure sample of N,N'-Bis[1-oxo-3-(1-adamantyl)propyl]-4,13-diaza-18-crown-6 was obtained by chromatography on a small column of $Al_2O_3$ (act. II-III) using 0→2% MeOH in $CH_2Cl_2$ as an eluent.

IR (KBr) v/cm$^{-1}$:2899 (s), 2845 (s), 1450 (m), 1350 (m), 1125 (s), 1071 (m).

$^1$H NMR (CDCl$_3$) δ/ppm: 1.35-1.45 (m, 4H), 1.47 (br. s, 12H), 1.60-1.75 (m, 12H), 1.95 (br. s, 6H), 2.25-2.35 (m, 4H), 3.55-3.70 (m, 24H).

$^{13}$C NMR (CDCl$_3$) δ/ppm: 26.18 (t, 1C), 26.30 (t, 1C), 28.29 (d, 6C), 31.65 (s, 2C), 36.80 (t, 6C), 39.19 (t, 1C); 39.22 (t, 1C), 41.88 (t, 6C), 46.45 (t, 1C), 46.77 (t, 1C), 48.44 (t, 1C), 48.62 (t, 1C), 69.09 (t, 1C), 69.67 (t, 1C), 69.78 (t, 1C), 70.07 (t, 2C), 70.20 (t, 1C), 70.41 (t, 1C), 70.59 (t, 1C), 173.86 (s, 1C), 173.91 (s, 1C).

HRMS calculated for $[C_{38}H_{62}N_2O_6+H]$ 643.4681. Found 643.4706.

Reduction of N-[1-oxo-3-(adamantyl)propyl)]aza-18-crown-6

By following the general reduction procedure, N-[3-(1-adamantyl)propyl]aza-18-crown-6 was obtained via reaction of N-[1-oxo-3-(adamantyl)propyl)]aza-18-crown-6 (0.5 g, 0.0011 mol) in 40 cm$^3$ of dry THF with $B_2H_6$ in THF (5.0 cm$^3$, 0.0025 mol). The crude product was purified via column chromatography on $Al_2O_3$ (act. II-III) using 0→2% MeOH in $CH_2Cl_2$ as an eluent, thereby yielding 0.124 g (25.6%) of yellowish oily product N-[3-(1-adamantyl)propyl]aza-18-crown-6.

Biological Assays
Test Procedures:

The described assay was used to test the effects of compounds on the proliferation of various human tumor cell lines, whereby cytostatic and cytotoxic effects on cells can be differentiated. The experiments were carried out on human cell lines, which were derived from 6 tumor types. The following cell lines were used: MCF-7 (breast carcinoma), SW 620 (colon carcinoma), HCT 116 (colon carcinoma), MOLT-4 (acute lymphoblastic leukemia), H 460 (lung carcinoma), HeLa (cervical carcinoma), MiaPaCa-2 (pancreatic carcinoma).

MCF-7, SW 620, HCT 116, HeLa, MiaPaCa-2 and H 460 cell lines were cultured as monolayers and maintained in Dulbecco's modified Eagle medium (DMEM), while MOLT-4 cells were cultured in suspension in nutritive medium RPMI 1640, both supplemented with 10% fetal bovine serum (FBS), 2 mM L-glutamine, 100 U/ml penicillin and 100 μg/ml streptomycin in a humidified atmosphere with 5% $CO_2$ at 37° C.

The panel cell lines were inoculated onto a series of standard 96-well microtiter plates on day 0, at $1 \times 10^4$ to $3 \times 10^4$ cells/ml, depending on the doubling times of the specific cell line. Test agents were added next day to the cell lines in five consecutive 10-fold dilutions ($10^{-8}$ to $10^{-4}$ M) and incubated for a further 72 hours. Working dilutions were freshly prepared on the day of testing. The solvent (DMSO) was also tested for eventual inhibitory activity by adjusting its concentration to be the same as in working concentrations. After 72 hours of incubation the cell growth rate was evaluated by performing the MTT assay (Mossman, Methods Immunol, 1983, 65, 55-63.), which detects dehydrogenase activity in viable cells. The MTT Cell Proliferation Assay is a colorimetric assay system, which measures the reduction of a tetrazolium component (MTT) into an insoluble formazan produced by mitochondria of viable cells. For this purpose the substance treated medium was discarded and MTT was added to each well in concentration of 20 μg/40 μl. After four hours of incubation the precipitates were dissolved in 160 μl of dimethylsulphoxide (DMSO). The absorbance (OD, optical density) was measured on a microplate reader at 570 nm. The absorbance is directly proportional to the cell viability. The percentage of growth (PG) of the cell lines was calculated according to one of the following two equations (according to the National Cancer Institute protocols, www.dtp.nci.nih.gov):

If (mean OD$_{test}$−mean OD$_{tzero}$)≧0 then

PG=100×(mean OD$_{test}$−mean OD$_{tzero}$)/(mean OD$_{ctrl}$−mean OD$_{tzero}$).

If (mean OD$_{test}$−mean OD$_{tzero}$)<0 then:

PG=100×(mean OD$_{test}$−mean OD$_{tzero}$)/OD$_{tzero}$.

where:
Mean OD$_{tzero}$=the average of optical density measurements before exposure of cells to the test compound.

Mean OD$_{test}$=the average of optical density measurements after the desired period of time.

Mean OD$_{ctrl}$=the average of optical density measurements after the desired period of time with no exposure of cells to the test compound.

Each test point was performed in quadruplicate in three individual experiments. The results were expressed as IC$_{50}$, a concentration necessary for 50% of proliferation inhibition. Each result is a mean value from three separate experiments. The IC$_{50}$ measures the growth inhibitory power of the test agent and represents the concentration that causes 50% growth inhibition. The IC$_{50}$ is calculated from dose-response curves using linear regression analysis by fitting the test concentrations that give PG values above and below the respective reference value (e.g. 50% of inhibition for IC$_{50}$). Therefore, a "real" value for any of the response parameters is obtained only if at least one of the tested drug concentrations falls above, and likewise at least one falls below the respective reference value. If however, for a given cell line or test agent all of the tested concentrations produce PGs exceeding the respective reference level of effect (e.g. PG value of 50%), then the highest tested concentration is assigned as the default value. In the screening data report the default value is preceded by a ">" sign.

The results presented in the Table 1 clearly show that the unsubstituted diaza crown-6 did not show any antiproliferative activity up to maximal tested concentration (c=100 μM) during 72 hours. Monoaza substituted compounds showed a more significant activity (IC$_{50}$ conc≈10-70 μM), while diaza-substituted compounds showed the most prominent activity (0.2-14 μM). In both cases the amide sidearm of macro ring obviously reduces the activity when compared to amine sidearm (in general the $IC_{50}$ were two to ten times lower for the letter compounds). Moreover, the length of alkyl chain strongly influences the activity, with propyl chain being more active than ethyl one.

TABLE 1

In vitro growth inhibition of various tumor cell lines by aza-crown compounds.

| Compound | Structure | $IC_{50}^{[a]}$ (μM) | | | | | | |
|---|---|---|---|---|---|---|---|---|
| | | H 460 | SW 620 | MCF-7 | MiaPaCa-2 | Hela | HCT 116 | MOLT-4 |
| Diaza-18-crown-6 | (structure: diaza-18-crown-6) | >100 | >100 | >100 | >100 | >100 | >100 | >100 |
| 1 | (structure: adamantyl-ethyl monoaza-18-crown-6) | 15 ± 0.6 | 9 ± 6 | 8 ± 4 | 12 ± 0.6 | 16 ± 0.5 | N.T. | N.T. |
| 2 | (structure: adamantyl-propyl monoaza-18-crown-6) | 15 ± 0.1 | 9 ± 3 | 6 ± 5 | 11 ± 2 | 14 ± 3 | N.T. | N.T. |
| 3 | (structure: adamantyl-acetamide monoaza-18-crown-6) | >100 | >100 | >100 | >100 | >100 | N.T.[b] | N.T. |
| 4 | (structure: adamantyl-propionamide monoaza-18-crown-6) | 72 ± 7 | 13 ± 2 | 17 ± 5 | 30 ± 3.4 | 28 ± 7 | N.T. | N.T. |
| 5 | (structure: bis(adamantyl-ethyl) diaza-18-crown-6) | 4 ± 3 | 2.6 ± 1.9 | 4 ± 0.7 | 1.7 ± 0.6 | 2.3 ± 1.4 | N.T. | N.T. |
| 6 | (structure: bis(adamantyl-propyl) diaza-18-crown-6) | 0.2 ± 0.3 | 1 ± 0.4 | 1 ± 0.4 | N.T. | N.T. | 0.4 ± 0.4 | 1 ± 1 |

TABLE 1-continued

In vitro growth inhibition of various tumor cell lines by aza-crown compounds.

| Compound | Structure | $IC_{50}^{[a]}$ (µM) | | | | | | |
|---|---|---|---|---|---|---|---|---|
| | | H460 | SW620 | MCF-7 | MiaPaCa-2 | Hela | HCT 116 | MOLT-4 |
| 7 | 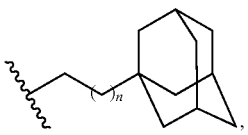 | 14 ± 1 | 12 ± 5 | 5 ± 2 | N.T. | N.T. | 6 ± 0 | 6 ± 6 |
| 8 | 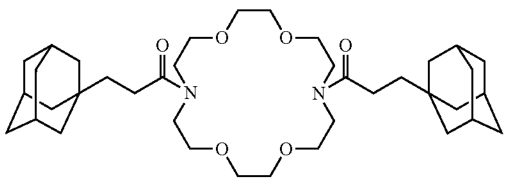 [SMILES: O=C(CCC12CC3CC(CC(C3)C1)C2)N1CCOCCOCCN(C(=O)CCC23CC4CC(CC(C4)C2)C3)CCOCCOCC1] | 11 ± 5 | 19 ± 16 | 2 ± 0.4 | N.T. | N.T. | 6 ± 4 | 3 ± 0.5 |

[a]$IC_{50}$-the concentration that causes 50% growth inhibition
[b]N.T. not tested

What is claimed is:

1. A compound having formula I:

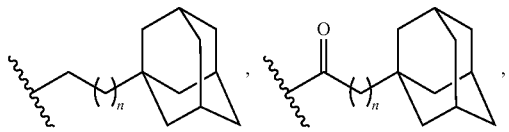

wherein R and R' are selected from the group comprising

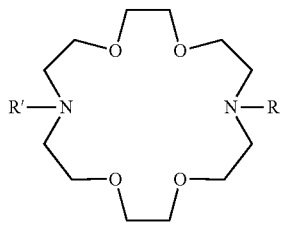

provided that R and R' cannot simultaneously be H; and n is an integer from 1 to 4.

2. The compound of claim 1, wherein R=R', and R and R' are selected from the group comprising:

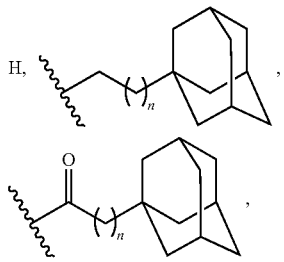

and n is an integer from 1 to 2.

3. The compound of claim 2, wherein R and R' are:

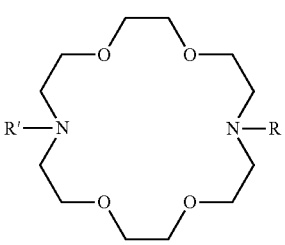

and n is an integer from 1 to 2.

4. The compound of claim 1, 2, or 3, in a pharmaceutically acceptable salt.

5. A pharmaceutical composition, comprising:
a compound having formula I:

wherein R and R' are selected from the group comprising

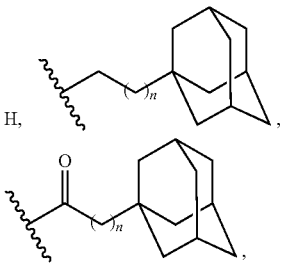

provided that R and R' cannot simultaneously be H; and n is an integer from 1 to 4;
and pharmaceutically acceptable salts thereof.

6. The pharmaceutical composition of claim 5, wherein R=R', and R and R' are selected from the group comprising:

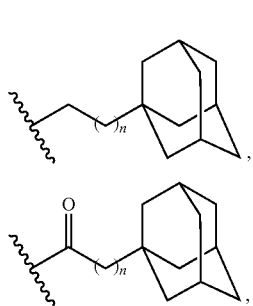

and n is an integer from 1 to 2.

7. The pharmaceutical composition of claim 6, wherein R and R' are:

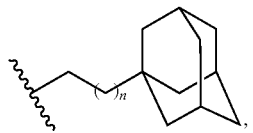

and n is an integer from 1 to 2.

8. A method of in-vitro inhibition of cancer cell growth, comprising administration of a compound having formula I:

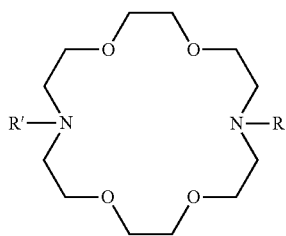

I wherein R and R' are selected from the group comprising

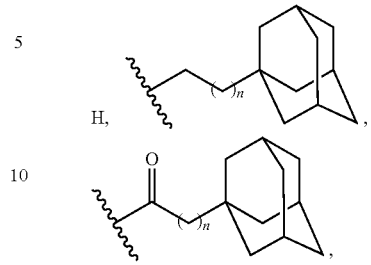

provided that R and R' cannot simultaneously be H; and n is an integer from 1 to 4;
or pharmaceutically acceptable salts thereof;
on human tumor cells in vitro to inhibit growth of the tumor cells.

9. The method of claim 8, wherein R=R', and R and R' are selected from the group comprising:

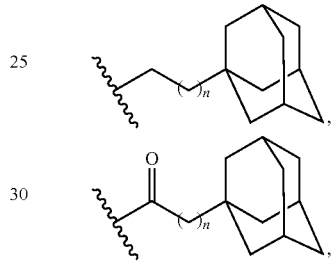

and n is an integer from 1 to 2.

10. The method of claim 8, wherein R and R' are:

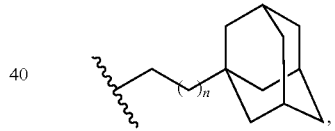

and n is an integer from 1 to 2.

* * * * *